US00PP34618P3

(12) United States Plant Patent
Olesen

(10) Patent No.: US PP34,618 P3
(45) Date of Patent: Oct. 4, 2022

(54) FLORIBUNDA ROSE PLANT NAMED 'POULPAL088'

(50) Latin Name: *Rosa hybrida*
Varietal Denomination: Poulpal088

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,633

(22) Filed: Sep. 7, 2021

(65) Prior Publication Data

US 2022/0104420 P1 Mar. 31, 2022

(30) Foreign Application Priority Data

Sep. 21, 2020 (QZ) ..... PBR 2020/2255

(51) Int. Cl.
*A01H 5/02* (2018.01)
*A01H 6/74* (2018.01)

(52) U.S. Cl.
USPC ..... Plt./141
CPC ..... *A01H 6/749* (2018.05)

(58) Field of Classification Search
USPC ..... Plt./101, 141
See application file for complete search history.

(56) References Cited

PUBLICATIONS https://online.plantvarieties.eu/publicSearch?denomination=poulpal088; Retrieved from the Internet on Oct. 25, 2021; citation for 'Poulpal088'.*

* cited by examiner

*Primary Examiner* — Susan McCormick Ewoldt

(57) ABSTRACT

A new garden rose plant of the Compact Floribunda class which has abundant, orange yellow bi-color flowers and attractive foliage. This new and distinct variety has shown to be uniform and stable in the resulting generations from asexual propagation.

2 Drawing Sheets

Botanical designation: *Rosa hybrida.*

Variety denomination: 'Poulpal088'.

This application claims priority to Plant Breeder's Rights Application Number 2020/2255, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpal088', originated as a single seedling from the stated cross.

The new variety may be distinguished from its male pollen parent and female seed parent primarily by the following characteristics. The male pollen parent plant has yellow flowers while the new variety has orange yellow bi-color flowers. The female seed parent plant has red flowers while the new variety has orange yellow bi-color flowers.

The objective of the hybridization of this rose variety was to create a new and distinct variety with unique qualities, such as:

1. Uniform and abundant orange yellow bi-color flowers;
2. Vigorous, but compact growth when propagated on its own roots;
3. Exceptional disease resistance.

This combination of qualities is not present in previously available commercial cultivars of this type, known to the inventor, and distinguish 'Poulpal088' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpal088' was selected in the spring of 2011 by the inventor as a single plant from the progeny of the aforementioned hybridization.

Asexual reproduction of 'Poulpal088' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpal088' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal088'.

Specifically illustrated in FIG. 1 of the drawings are open flowers viewed from above and the side, detached flower petals, sepals detached showing receptacle and reproductive flower parts.

Figure 1:
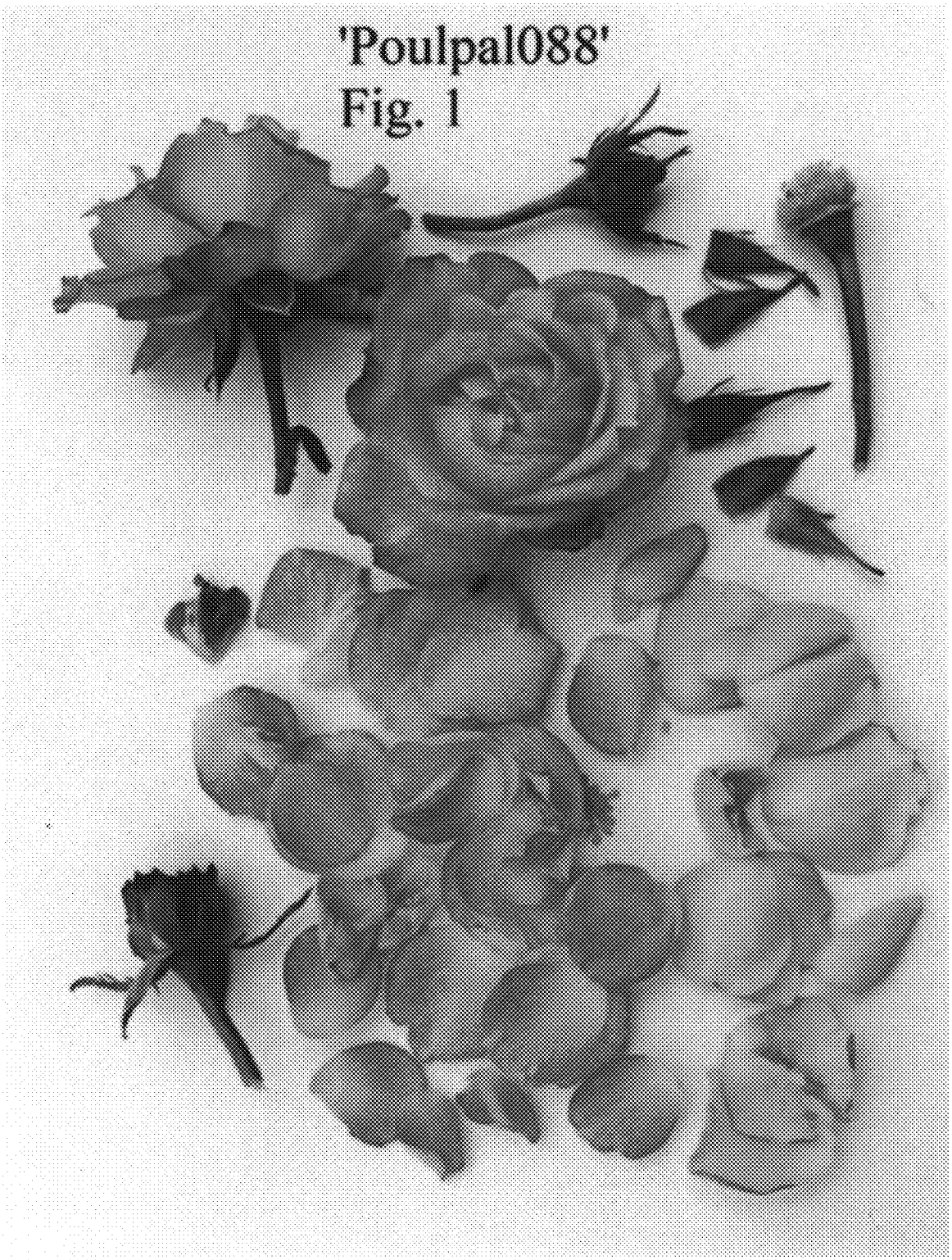
Figure 2:
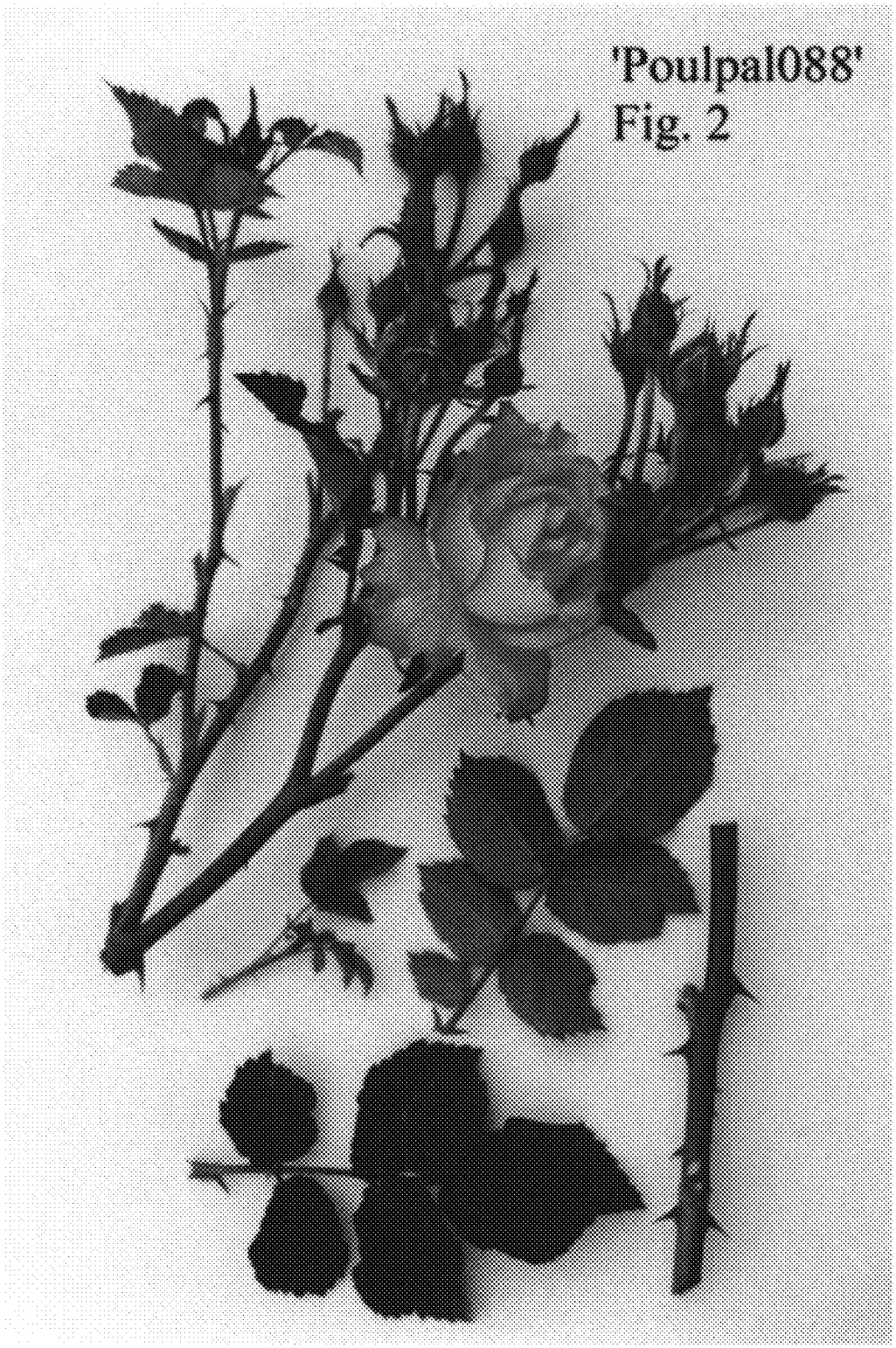

Specifically illustrated in FIG. 2 of the drawings is a cluster of open flowers on a branch, bare stems, mature and juvenile leaves.

Plants shown are 1 year old.

DETAILED DESCRIPTION OF THE VARIETY

The following is a description of 'Poulpal088', as observed in its growth in an open air container nursery in Odense Denmark. Observed plants are 1 year old and were grown on their own roots in 24 cm containers. Color references are made using The Royal Horticultural Society (London, England) Colour Chart, 2001, except where common terms of color are used.

For a comparison, several physical characteristics of the rose variety 'Poulpal037', U.S. Plant Pat. No. 24,488 are compared to 'Poulpal088' in Chart 1.

CHART 1

| | 'Poulpal088' | 'Poulpal037' |
|---|---|---|
| Petal Count | 65 to 70 | 30 |
| Flower Diameter | 70 mm | 55 mm |
| General Tonality of Flower Color | Yellow-Orange Group 16B, Orange Group 29B, and Red Group 43C. | Yellow-Orange Group 15C with other intonations of Red-Purple Group N66A. |

Flower and flower bud:

*Blooming habit.*—Continuous.

*Flower bud.*—Size: Upon opening, 23 mm in length from base of receptacle to end of bud. Bud diameter is 19 mm. Bud form: Urceolate. Bud color: As sepals divide petals are Greyed-Purple Group N186A, Orange-Red Group N34A, and Red Group 45C. Sepal inner surface: Color: Yellow-Green Group 146D. Surface: Lightly pubescent. Sepal outer surface: Color: Yellow-Green Group 144A with intonations of Greyed-Red Group 181B. Texture: Smooth. Sepal Shape: Apex: Cirrhose. Base: Flat at union with receptacle. Sepal Margin: Margins have strong foliaceous appendages on three of the five sepals. Sepal size: 30 mm long, 10 mm wide. Receptacle: Texture: Smooth. Size: 8 mm in height, 10 mm wide. Color: Yellow-Green Group 144A with intonations of Greyed-Purple Group 183D. Shape: Campanulate. Pedicel: Surface: Smooth. Length: 30 mm. Diameter: 3 mm on average. Color: Yellow-Green Group 144A with intonations of Greyed-Red Group 181A. Strength: Strong. Peduncle: Length: 3 to 10 cm. Diameter: About 4 mm. Color: Yellow-Green Group 144A with intonations of Greyed-Red Group 181A. Texture: Somewhat rough with stipitate glands.

*Flower bud development.*—Flower buds are borne in clusters of 3 to 9 flower buds per stem. Development as a panicle.

*Flower bloom.*—Fragrance: Moderate to strong perfume. Duration: The blooms have a duration on the plant of approximately 15 days. Petals fall cleanly away from plant after flowers have fully matured. Size: Flower diameter is 70 mm when open. Flower depth is 40 mm. Flower shape: Tea. Shape of flower, side view: The upper portion is flat convex. The lower portion is concave.

*Petalage.*—Under normal conditions, flowers have about 65 to 70 petals.

*General tonality of flower.*—Open flowers are Yellow-Orange Group 16B, Orange Group 29B, and Red Group 43C.

*Petal color.*—Upon opening, outer petals: Upper surface: At the basal zone Yellow Group 7A. Yellow-Orange Group 19B at the middle to marginal zone. The margins are Red Group 45B. Lower surface: Yellow-Orange Group 18B, splashed with Yellow Group 12C and other spotted intonations of Red Group 53D. Upon opening, inner petals: Upper surface: Yellow 12A at the base. Middle zone is Orange-Red Group 31A. At marginal zone splashed with Red Group 45B. Lower surface: Yellow Group 12B with intonations of Orange-Red Group 35B at margins. After opening, outer petals: Upper surface: The basal zone is Yellow Group 8A. Splashed with Red Group 51A at the middle and marginal zone. Lower surface: The basal zone is Yellow Group 10C. The middle and marginal zones are splashed with Red Group 53D. After opening, inner petals: Upper surface: The basal zone is Yellow Group 8A. Splashed with Red Group 51A at the middle and marginal zone. Lower surface: The basal zone is Yellow Group 10C. The middle and marginal zones are splashed with Red Group 53D.

*Petals.*—Petal Reflex: Somewhat reflexed at the margins. Margin: Entire with strong undulations. Shape: Round. Apex shape: Rounded. Base shape: Acute and obtuse. Size: 42 mm (l)×40 mm (w). Texture: Smooth. Thickness: Average.

*Reproductive flower parts.*—Pollen: None observed. Anthers: Size: 2 mm in length. Color: Yellow Group 12D. Quantity: 48 on average. Filaments: Color: Yellow Group 13A. Length: 5 mm. Pistils: Length: 10 mm. Quantity: 35 on average. Stigmas: Color: Greyed-Yellow Group 160C. Styles: Color: Green-White Group 157A. Location of stigmas: Superior in location relative to the length of the filaments and the height of the anthers. Hips: None Observed.

Plant:

*Plant growth.*—Upright, very compact, and bushy. Plants are 43 cm in height, and 35 cm wide.

*Stems.*—Color of juvenile growth: Yellow-Green Group 144A. Color of mature growth: Yellow-Green Group 144A with intonations of Greyed-Purple Group 183B. Length: Canes are about 20 cm from the base of the plant to the flowering portion. Diameter: About 6 mm. Internodes: On mature canes about 40 mm between nodes. Surface Texture: Young wood: Rough with small prickles. Older wood: Smooth.

*Long prickles.*—Incidence: 7 to 9 prickles per 10 cm of stem. Size: Average length of prickles on mature stems is 9 mm. Shape: Upper portion is linear. Lower portion is concave. Color: Juvenile prickles: Greyed-Purple Group 183A. Mature prickles: Greyed-Purple Group 183A.

*Plant foliage.*—Compound leaf: 135 mm (l)×95 (w). Quantity: 2 leaves per 10 cm of stem on average. Leaf bearing angle to the stem: 45 degrees. Color of juvenile foliage: Upper side: Yellow-Green Group 144A with intonations of Greyed-Purple Group 183A. Lower side: Yellow-Green Group 144A. Color of mature foliage: Upper side: Yellow-Green Group 147A. Lower side: Yellow-Green Group 147B.

*Plant leaves and leaflets.*—Stipules: Size: 14 mm long, 5 mm wide. Quantity: 2 per compound leaf. Shape: Linear, slightly broad based with outward extending apices. Margins: Finely serrated. Color: Yellow-Green Group 144A. Petiole: Length: 23 mm. Diameter: 2 mm. Upper surface color: Yellow-Green Group 144B with intonations of Greyed-Purple Group 187B. Lower surface color: Yellow-Green Group 144A. Rachis: Length: 43 mm. Upper surface color: Yellow-Green Group 144A with intonations of Greyed-Purple Group 187B. Lower surface color: Yellow-Green Group 144A with intonations of Greyed-Purple Group 183C. Leaflet: Quantity: 5 to 7 leaflets. Margins: Serrated. Size: Terminal leaflets are about 60 mm long, 43 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

*Disease resistance.*—Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

*Cold hardiness.*—The variety is tolerant to USDA Cold Hardiness Zone 6.

*Heat tolerance.*—The variety has been found to be suitable for climate conditions found in the American Horticulture Society heat zone 7.

I claim:

1. A new and distinct variety of rose plant of the Compact Floribunda rose class named 'Poulpal088', substantially as illustrated and described herein, due to its abundant orange yellow bi-color flowers, disease resistance, and extended period of bloom.

* * * * *

'Poulpal088'

'Poulpal088'